United States Patent [19]
Gee et al.

[11] Patent Number: 5,776,454
[45] Date of Patent: Jul. 7, 1998

[54] PERMANENT WAVING WITH MERCAPTOSILICONES

[75] Inventors: Ronald Paul Gee; Carol Anne Hoag, both of Midland, Mich.

[73] Assignee: Dow Corning Corporation, Midland, Mich.

[21] Appl. No.: 713,910

[22] Filed: Sep. 13, 1996

[51] Int. Cl.⁶ .................................. A61K 7/09; A61K 7/06
[52] U.S. Cl. .................... 424/70.5; 424/70.12; 132/204
[58] Field of Search ..................... 424/70.5, 70.12; 132/204

[56] References Cited

U.S. PATENT DOCUMENTS

| | | | |
|---|---|---|---|
| 4,770,873 | 9/1988 | Wolfram | 424/71 |
| 5,270,036 | 12/1993 | Varaprath | 424/71 |
| 5,279,818 | 1/1994 | Halloran | 424/71 |
| 5,300,285 | 4/1994 | Halloran | 424/71 |
| 5,362,485 | 11/1994 | Hayama | 424/70 |

FOREIGN PATENT DOCUMENTS

| | | |
|---|---|---|
| 807628 | 3/1969 | Canada. |
| 295780 | 12/1988 | European Pat. Off.. |
| 459500 | 12/1991 | European Pat. Off.. |
| 463431 | 1/1992 | European Pat. Off.. |

*Primary Examiner*—Sally Gardner-Lane
*Attorney, Agent, or Firm*—James L. DeCesare

[57] ABSTRACT

A process for permanent waving of hair by a reaction in which cystine bridges are reduced to cysteine, the hair reshaped, and the reaction reversed. The improvement in the process resides in the step of reducing or reversing the reaction by applying to hair a composition which includes an emulsion polymerized mercapto functional silicone. Permanent hair waving with waving lotions, neutralizing solutions, or both, containing such emulsion polymerized mercapto functional silicones, provide waved hair with improved conditioning benefits.

10 Claims, No Drawings

PERMANENT WAVING WITH MERCAPTOSILICONES

BACKGROUND OF THE INVENTION

This invention is directed to a method of waving hair, and to silicone containing waving lotions and neutralizing solutions which are useful in permanent waving human hair.

Keratin is a fibrous protein composed of eighteen different kinds of amino acids. It is widely distributed in hair and constitutes the major component thereof. Keratin is characterized by a crosslinked structure having one disulfide bond —S—S— per average 10–20 amino acid residues. It is most frequently represented as cystine which has the formula $HO_2CC(NH_2)HCH_2S$—$SCH_2C(NH_2)HCO_2H$.

The first basic step in a permanent waving process is the partial reduction of cystine $HO_2CC(NH_2)HCH_2S$—$SCH_2C(NH_2)HCO_2H$ to cysteine $HO_2CC(NH_2)HCH_2SH$. Typically, a waving lotion containing a reducing agent such as thioglycolic acid is used in this step in a reaction in which cystine bridges are reduced to cysteine. After the hair has been reshaped, this reaction is reversed by application to the hair of a neutralizer which is a solution containing an oxidizing agent such as hydrogen peroxide. Cysteine residues formed during the reduction step are converted back into cystine upon neutralization.

There exists a need in the art for alternative forms of permanent waving lotions and neutralizing solutions. The present invention meets this need and provides silicone containing waving compositions found to impart to hair improved and unexpected benefits, such as conditioning of the hair, resulting in waved hair that feels smoother and silkier, and which has improved combing properties.

BRIEF SUMMARY OF THE INVENTION

The invention relates to a hair waving process and to waving compositions for use in the waving process. More particularly, a silicone containing waving lotion is used to reduce cystine bridges to cysteine during the reduction phase of the permanent waving process. The waving lotion of the present invention includes an emulsion polymerized mercapto functional silicone, a reducing agent such as thioglycolic acid, and a carrier fluid.

When used in conjunction with thioglycolic acid containing waving lotions, the waving lotion of our invention possesses the advantage of imparting to the hair conditioning benefits during the waving process.

The invention also relates to a silicone containing neutralizing solution, employed to reform cystine from cysteine produced during the reduction phase of the permanent waving process. The neutralizing solution of the present invention includes the emulsion polymerized mercapto functional silicone, an oxidizing agent such as hydrogen peroxide, and a carrier fluid.

When used in conjunction with hydrogen peroxide containing neutralizing solutions, the neutralizing solution of our invention also imparts conditioning benefits to the hair.

These and other features and objects of our invention will become apparent from a consideration of the detailed description.

DETAILED DESCRIPTION

According to our invention, mercapto functional silicone emulsions are prepared, most preferably, by emulsion polymerization techniques described in European Patent Application 0 459 500, published Dec. 4, 1991, and in particular, to the use of such silicone-containing emulsions in permanent waving lotions and/or permanent waving neutralizing solutions, to provide beneficial conditioning properties to hair.

To prepare the emulsion, mercaptoalkyl alkoxysilanes are copolymerized with a cyclic polysiloxane in emulsion polymerization, to form white opaque emulsions, translucent, or clear microemulsions. These emulsions and microemulsions may be cationic or anionic. When these emulsions and microemulsions are included in permanent waving lotions, and optionally in the permanent waving neutralizing solution, they provide improved combing and feel characteristics, when compared to control formulations without silicones, or in waving treatments with polydimethylsiloxane-type mechanical emulsions.

Emulsions produced by this emulsion polymerization technique typically contain silicone concentrations of 10–70 percent by weight of the total emulsion solution. The preferred level of silicone is 25–60 percent by weight. The larger the particle size, the higher the concentration of silicone the emulsion may contain. Emulsions may be produced containing less than 10 percent by weight of silicone, however, such emulsions typically hold little or no economic value.

While mercapto functional silicones can be made by emulsion polymerization techniques other than those specifically described in EP 459500, preparation of these emulsion polymers by the emulsion polymerization process in EP 459500 is preferred, due to its economic advantage and high degree of particle size control.

The mercapto functional silicone of our invention can be represented by the formula:

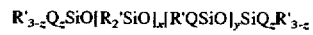

where R' denotes an alkyl group of 1–4 carbon atoms or a phenyl group, provided at least 50 percent of the total number of R' groups are methyl. Q denotes a mercapto functional substituent —R"SH where R" is a divalent alkylene radical of 3–6 carbon atoms; z is 0 or 1; x has an average value of 25–500; y is 0–50 when z is 1, and y has an average value of 1–50 when z is 0.

Suitable R' groups are methyl, ethyl, propyl, isopropyl, butyl, isobutyl, and phenyl. The alkylene radicals R" include trimethylene, tetramethylene, pentamethylene, —$CH_2CHCH_3CH_2$—, and —$CH_2CH_2CHCH_3CH_2$—. Silicones where R" is a trimethylene or an alkyl substituted trimethylene radical such as —$CH_2CHCH_3CH_2$— are preferred.

When z is zero, the silicone polymer has only pendent mercapto functional substituents in the polymer chain. When z is one, the silicone polymer may have only terminal mercapto functional substituents, or both terminal and pendent mercapto functional substituents in the polymer chain. While x can have a value greater than 500, i.e., up to 4,000 for example, preferably x varies from 25–500, and y varies from 0–50 when z is one and from 1–50 when z is zero. Most preferably, the value of x+y is about 50–300.

The mercapto functional silicone may be a linear polysiloxane or a branched-chain polysiloxane. Linear polysiloxanes correspond to the structural type $MD_nM$ or $R_3SiO(R_2SiO)_nSiR_3$. Branched-chain polysiloxanes contain at least one trifunctional $RSiO_{3/2}$ or tetrafunctional $SiO_{4/2}$ siloxane unit as a branching center. The branching unit is incorporated into the chain.

An example of a linear polysiloxane is:

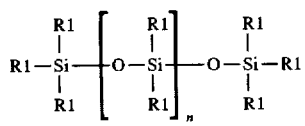

An example of a simple branched-chain polysiloxane is:

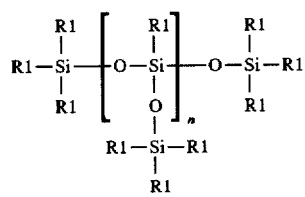

An example of a more complex branched-chain polysiloxane is:

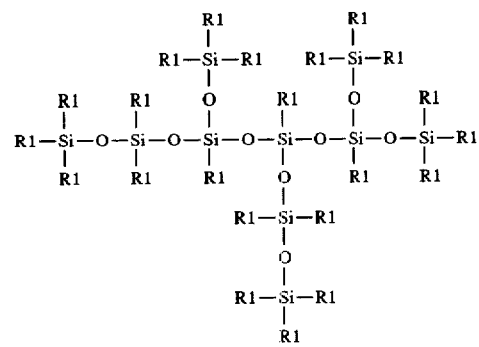

The permanent waving lotion includes as essential ingredients an emulsion containing an emulsion polymerized mercapto functional silicone, a reducing agent such as thioglycolic acid, and a suitable carrier fluid for delivering these active ingredients. The waving lotion may additionally contain wetting and foaming agents to improve spreading and retention of the waving lotion on the hair, as well as other types of conditioning agents to enhance a smooth texture, improve ease of combing, and to increase control of fly-away.

The permanent waving lotion should contain 1.0 to 10.0 percent by weight of the emulsion containing the emulsion polymerized mercapto functional silicone, 0.1 to 10.0 percent by weight of the reducing agent, and 80.0 to 99.8 percent by weight of carrier fluid.

The neutralizing solution includes as its essential ingredients the emulsion containing the emulsion polymerized mercapto functional silicone, an oxidizing agent such as hydrogen peroxide, and suitable carrier fluid for delivering these active ingredients. Like the waving lotion, the neutralizing solution may additionally contain wetting and foaming agents to improve spreading and retention of the neutralizing solution on the hair, as well as other types of conditioning agents to enhance a smooth texture, improve ease of combing, and to increase control of fly-away.

The neutralizing solution should contain 1.0 to 10.0 percent by weight of the emulsion containing the emulsion polymerized mercapto functional silicone, 0.1 to 5.0 percent by weight of the oxidizing agent, and 85.0 to 99.8 percent by weight of carrier fluid.

As carrier fluid, there may be used alcohols, hydrocarbons, halogenated hydrocarbons, water, mixtures of alcohol and water, or volatile silicones. Representative carrier fluids are water, ethanol, isopropyl alcohol, mineral spirits, trichloroethane, and dichlorotetrafluoroethane.

The permanent waving lotion and the neutralizing solution may contain other ingredients in addition to the mercapto functional silicone, the reducing agent, the oxidizing agent, and the carrier fluid. For example, adjuvants common to permanent waving lotions and neutralizing solutions may be employed, such as coloring agents, perfumes, oils, opacifiers, surfactants, and cationic resins.

The waving lotion and the neutralizing solution of our invention is suitable for use in permanent waving processes which may be characterized as hot wave processes, mild wave processes, and cold wave processes. In a typical cold wave process for example, the hair is first shampooed, and the freshly shampooed and still damp hair is divided into about forty to sixty tresses. Each tress is wetted with the waving lotion and wound onto plastic curlers. The size of the curler determines the nature of the resultant wave. Small curlers, for example, result in tighter waves. The hair is rinsed thoroughly, and neutralized with the neutralizing solution. The hair is then unwound, rinsed again, and either dried or set into a desired style.

The following examples are set forth for the purpose of illustrating the invention in more detail. Emulsions were prepared in Examples I–III by the emulsion polymerization process according to EP 459500. The emulsions prepared in Examples II and III were used in studies evaluating the addition of various types of silicone emulsions to permanent waving lotions and permanent waving neutralizing solutions, and their effect on treated hair tresses. In tests where the emulsions in Examples II and III were added at 5 percent by weight to both the permanent waving lotion and the permanent waving neutralizing solution, the emulsion containing the emulsion polymerized mercapto functional silicone prepared in Example II was rated in the best (1) category for dry combing by 4 out of 5 panelists, in comparison to (i) an emulsion containing an amino functional silicone of the type described in U.S. Pat. No. 4,770,873 (Sep. 13, 1988), and (ii) a mechanically prepared emulsion containing a mercapto functional silicone according to European Patent Application 0 295 780, published Dec. 21, 1988. Our emulsion containing the emulsion polymerized mercapto functional silicone of Example II was also rated in the best (1) category for dry feel by 5 out of 5 panelists, again in comparison to (i) the emulsion containing the amino functional silicone of the type described in U.S. Pat. No. 4,770,873 (Sep. 13, 1988), and (ii) the mechanically prepared emulsion containing the mercapto functional silicone according to European Patent Application 0 295 780, published Dec. 21, 1988.

EXAMPLE I

In this example of emulsion polymerization, a cationic emulsion containing 35 percent by weight of a one mole percent emulsion polymerized mercapto functional silicone polymer was prepared using the ingredients shown below. The particle size of the silicone in the emulsion was 172 nanometers.

| Ingredients | Weight Percent | Weight (grams) |
|---|---|---|
| Water | 34.00 | 238.00 |
| RENEX 30 | 2.80 | 19.60 |
| ARQUAD 16-29 | 1.83 | 12.81 |

| Ingredients | Weight Percent | Weight (grams) |
|---|---|---|
| Octamethylcyclo tetrasiloxane [(CH$_3$)$_2$SiO]$_4$ | 34.41 | 240.87 |
| 3-mercaptopropyl trimethoxysilane HSCH$_2$CH$_2$CH$_2$Si(OMe)$_3$ | 0.91 | 6.37 |
| Rinse water | 0.50 | 3.50 |
| 50% NaOH aqueous | 0.40 | 2.80 |
| Rinse water | 0.50 | 3.50 |
| Glacial acetic acid | 0.33 | 2.31 |
| Rinse water | 0.50 | 3.50 |
| Dilution water | 23.77 | 166.39 |
| Biocide | 0.05 | 0.35 |
| Total | 100.00 | 700.00 |

To a one liter flask was added 238.00 g of water, 19.60 g of RENEX 30 (a tridecyl poly-12-oxyethylene nonionic surfactant sold by ICI Surfactants, Wilmington, Del.), and 12.81 g of ARQUAD 16–29 (a 29 percent by weight aqueous solution of cetyltrimethylammonium chloride cationic surfactant sold by Akzo Chemicals Inc., Chicago, Ill.). The flask was fitted with a glass rod and TEFLON® paddle stirrer, reflux condenser, heating mantle, and a thermocouple attached to a temperature controller. The contents of the flask were stirred to dissolve the two surfactants. The stirrer was set to about 300 RPM (31.4 radians per second), 240.87 g of octamethylcyclotetrasiloxane was added, and the flask was heated to 90 degrees Centigrade. When the temperature was stable at 90° C., 6.37 g of 3-mercaptopropyltrimethoxysilane was added. The vial containing the silane was rinsed with 3.50 g water and added. 2.80 g of 50 percent NaOH was added, and the vial containing the NaOH was rinsed with 3.50 g of water and added. The flask was held at 90° C. with stirring for 6 hours. The reaction was neutralized by adding 2.31 g of acetic acid, the vial containing the acid was rinsed with 3.50 g of water and added to flask, and then the flask was allowed to cool. The remaining 166.39 g of water was added, and 0.35 g of KATHON CG/ICP was added when the temperature was below about 50° C. KATHON CG/ICP is 5-chloro-2-methyl-4-isothiazolin-3-one, a biocide and antimicrobial sold by Rohm & Haas Company, Philadelphia, Pa., for in-container products, with EPA Reg. 707-161. The product of this example was a white emulsion containing a mercapto functional silicone with a particle size of 172 nanometers.

EXAMPLE II

This example illustrates an emulsion polymerization method for preparing an emulsion containing a 0.5 mole percent mercaptopropyl functional branched polydimethylsiloxane by combining the ingredients shown below.

| Ingredients | Weight Percent | Weight (grams) |
|---|---|---|
| Water | 34.00 | 102.00 |
| RENEX 30 | 2.80 | 8.40 |
| ARQUAD 16–29 | 1.83 | 5.49 |
| Octamethylcyclo tetrasiloxane | 34.41 | 103.23 |
| 3-mercaptopropyl trimethoxysilane | 0.46 | 1.38 |
| Rinse water | 0.50 | 1.50 |
| 50% NaOH aqueous | 0.40 | 1.20 |
| Rinse water | 0.50 | 1.50 |
| 10% aqueous acetic acid | 3.50 | 10.50 |
| Dilution water | 21.55 | 64.65 |
| Biocide | 0.05 | 0.15 |
| Total | 100.00 | 300.00 |

To a one liter flask was added 102.00 g of water, 8.40 g of RENEX 30, and 5.49 g of ARQUAD 16–29. The flask was fitted with a glass rod and TEFLON® paddle stirrer, reflux condenser, heating mantle, and a thermocouple attached to a temperature controller. The contents of the flask were stirred to dissolve the two surfactants. The stirrer was set to about 300 RPM (31.4 radians per second), and 103.23 g of octamethylcyclotetrasiloxane was added. The flask was heated to 90 degrees Centigrade. When the temperature was stable at 90° C., 1.38 g of 3-mercaptopropyltrimethoxysilane was added. The vial containing the silane was rinsed with 1.50 g of water and added to the flask. 1.20 g of 50 percent NaOH was added, and the vial containing the NaOH was rinsed with 1.50 g of water and added to the flask. The flask was held at 90° C. with stirring for 4 hours. Samples in 25 g portions were taken at intervals of 1, 2, 3, and 4 hours. The reaction was neutralized by adding 6.99 g of 10 percent aqueous acetic acid solution. The vial containing the acid was rinsed with a portion of the 43.07 g of dilution water and added to flask. The flask was then allowed to cool. The remaining dilution water was added, and 0.09 g of KATHON CG/ICP biocide was added when the temperature was below about 50° C. The product from this example was a white emulsion containing a branched mercapto functional silicone with a particle size of 163 nanometers. This emulsion was used to prepare a permanent waving lotion and neutralizing solution shown in Tables I and II as "C - Branched".

EXAMPLE III

This example illustrates another emulsion polymerization method for the preparation of an emulsion containing a 0.5 mole percent mercaptopropyl functional linear polydimethylsiloxane by combining the ingredients shown below.

| Ingredients | Weight Percent | Weight (grams) |
|---|---|---|
| Water | 34.00 | 102.00 |
| RENEX 30 | 2.80 | 8.40 |
| ARQUAD 16–29 | 1.83 | 5.49 |
| Octamethylcyclo tetrasiloxane | 34.41 | 103.23 |
| 3-mercaptopropylmethyl dimethoxysilane HSCH$_2$CH$_2$CH$_2$SiMe(OMe)$_2$ | 0.42 | 1.26 |
| Rinse water | 0.50 | 1.50 |
| 50% NaOH aqueous | 0.40 | 1.20 |
| Rinse water | 0.50 | 1.50 |
| 10% aqueous acetic acid | 3.50 | 10.50 |
| Dilution water | 21.59 | 64.77 |
| Biocide | 0.05 | 0.15 |
| Total | 100.00 | 300.00 |

To a one liter flask was added 102.00 g of water, 8.40 g of RENEX 30, and 5.49 g of ARQUAD 16–29. The flask was fitted with a glass rod and TEFLON® paddle stirrer, reflux condenser, heating mantle, and a thermocouple attached to a temperature controller. The contents of the flask were stirred to dissolve the two surfactants. The stirrer was set to about 300 RPM (31.4 radians per second), and 103.23 g of octamethylcyclotetrasiloxane was added while heating the flask to 90 degrees Centigrade. When the temperature was stable at 90° C., 1.26 g of 3-mercaptopropylmethyldimethoxysilane was added. The vial containing the silane was rinsed with 1.50 g of water and added to the flask. 1.20 g of 50 percent NaOH was added to the flask, and the vial containing the NaOH was rinsed with 1.50 g of water and added to the flask. The flask was held at 90° C. with stirring for 4 hours. Samples in 25 g portions were taken at intervals of 1, 2, 3, and 4 hours. The reaction was neutralized by adding 6.99 g of 10 percent aqueous acetic acid solution. The vial containing the acid was rinsed with a small portion of the 43.13 g of dilution water and added to flask. The flask was then allowed to cool. The remaining dilution water was added, and 0.09 g of KATHON CG/ICP biocide was added to the flask when the temperature was below about 50° C. The product from this example was a white emulsion containing a linear mercapto functional silicone with a particle size of 138 nanometers. This emulsion was used to prepare a permanent waving lotion and neutralizing solution shown in Tables I and II as "D - Linear".

EXAMPLE IV

To compare our invention with the invention described in European Patent Application 0 295 780, published Dec. 21, 1988, a mechanical emulsion containing a mercapto functional silicone was prepared from the following ingredients:

| | Ingredient | Parts | Weight (grams) |
|---|---|---|---|
| 1. | (mercaptopropyl)methylsiloxane dimethylsiloxane copolymer | 35.0 | 350.0 |
| 2. | TERGITOL ® TMN-6 | 1.92 | 19.2 |
| 3. | TRITON ® X-405 | 2.26 | 22.6 |
| 4. | Water | 60.82 | 608.2 |
| | Total | 100 | 1,000 |

The copolymer was a fluid (Code SMS-022) sold commercially by Gelest Inc., Tully Town, Pa. According to the manufacturer, the fluid has a viscosity between 160–200 centistokes ($mm^2/s$), a molecular weight between 8,000–10,000, and 2–3 mole % (mercaptopropyl) methylsiloxane. Based on Gelest's general information, the copolymer has the formula $Me_3SiO(Me_2SiO)_{114}(MeQSiO)_3SiMe_3$ where Me is methyl and Q is —$CH_2CH_2CH_2SH$. This structure has a molecular weight of about 9,000, and 2.5 mole % (mercaptopropyl) methylsiloxane, which corresponds to the Gelest product description.

The Gelest copolymer would correspond almost identically to Compound A in EP 295780, which has unit values of 98 and 2; compared to corresponding unit values of 114 and 3, respectively, in Gelest's fluid.

TERGITOL® TMN-6 is a trademark of Union Carbide Corporation, Danbury, Conn., for their nonionic surfactant which is an ethoxylated trimethylnonanol. TRITON® X-405 is also a trademark of Union Carbide for another nonionic surfactant which is an octylphenoxypolyethoxyethanol.

A mechanical emulsion of the copolymer was prepared by adding the two surfactants to water, and mixing until the surfactants were dissolved. The copolymer was then added to a 2,000 milliliter plastic beaker containing the water solution of the surfactants. A hazy opaque emulsion formed that was gray and murky instead of white and milky. The emulsion was stirred at about 350 RPM (36.6 radians per second), for 30 minutes. It was then passed through a homogenizer at 7,000 psi (48,264 kPa) which provided an emulsion containing the copolymer as particles with an average diameter of 492 nanometers. The emulsion was passed through the homogenizer a second time at 7,000 psi (48,264 kPa) which provided an emulsion containing the copolymer as particles with an average diameter of 426 nanometers. A third pass of the emulsion through the homogenizer at 7,000 psi (48,264 kPa) provided an emulsion containing the copolymer as particles with an average diameter of 437 nanometers. The emulsion was milky white after the first pass through the homogenizer. After the third pass of the emulsion through the homogenizer, 933.5 grams of a mechanical emulsion containing the mercapto functional silicone copolymer was recovered.

This mechanical emulsion was used in the permanent waving lotion and permanent waving neutralizing solution tested in Tables I and II. It is shown in the Tables as "A - EP295780".

To differentiate our invention as represented by Examples I–III from the invention described in EP 295780 as represented by Example IV, it should be noted that there is a significant difference between the technique of preparing mechanical emulsions, and the technique of preparing emulsions by emulsion polymerization.

In general, reference may be had to European Patent Application 0 463 431 published Jan. 2, 1992, for techniques of preparing emulsions mechanically, and to EP 459500 for techniques for preparing emulsions by emulsion polymerization.

Mechanical emulsions are prepared by mixing a silicone polymer or copolymer in water with one or more surfactants, and subjecting the mixture to high shear. Anionic, nonionic, and cationic, surfactants are employed to help stabilize these emulsions. For improved stability, it is often advantageous to use mixtures of two or more surfactants, i.e., combinations of two nonionic surfactants, an anionic and a nonionic surfactant, or a cationic and nonionic surfactant. Typically, from one to thirty parts by weight of surfactant are used per one hundred parts by weight of the silicone polymer or copolymer.

In emulsion polymerization, in contrast, there is combined a reactive silicone oligomer, a surfactant, a polymerization catalyst, and water. This mixture is stirred, and the silicone oligomers are allowed to polymerize until an emulsion is formed. Typically, alkoxysilanes or cyclic polysiloxanes are used as reactive monomers and oligomers. Combinations of silicone reactants can be used where it is desired to form copolymeric siloxanes in the resulting emulsion.

The following examples are set forth to illustrate the details of the testing protocols employed to evaluate the types of emulsions prepared in Examples I–IV in permanent waving applications.

EXAMPLE V

This example relates to procedures used in the treatment of hair tresses prior to their evaluation by a sensory panel. Hair tresses were prepared from 2.35–2.50 grams of slightly bleached virgin brown European hair which was weighed out. ½ inch (1.27 cm) of hair was cut off from the root end of the hair. Half of a plastic tab was sanded. Glue was placed in the center of the sanded portion of the plastic tab. The hair was placed on top of the glue, and more glue was placed on top of the hair. Another plastic tab was used to spread the hair and glue evenly on the tab, making sure to keep the hair ⅛ to ¼ inch (0.32 cm to 0.64 cm) from the sides of the tab. The tress was allowed to dry overnight. The tress was combed through once, and cut 6 inches (15.2 cm) from the bottom of the tab.

The next step in the procedure was to wash the hair tress with a blank shampoo. In this procedure, the tress was wet under 40° C. tap water for 15 seconds. 2.00 grams of a blank shampoo constituted by 15 percent by weight of ammonium lauryl sulfate and 85 percent by weight of water was applied to the tress. The shampoo was stroked through the tress for 30 seconds. The tress was rinsed under 40° C. tap water for 30 seconds. Again, 2.00 grams of the blank shampoo was applied and stroked through the tress for 30 seconds. The tress was then rinsed under 40° C. tap water for 1 minute. The tresses were then placed on a towel covered tray to dry overnight.

EXAMPLE VI

This example relates to the permanent waving procedures used in the treatment of hair tresses from Example V prior to their evaluation by a sensory panel. In this procedure, 5 percent by weight of the test material (i.e., a silicone containing emulsion) was added to both a permanent waving lotion and permanent waving neutralizing solution. The waving lotion contained thioglycolic acid in water, adjusted to a pH of 9.5 with a strong base. The neutralizing solution contained hydrogen peroxide in water adjusted to a pH of 3.4–3.7 with phosphoric acid. The neutralizing solution contained a small amount of an organic conditioning agent. The hair was wet under 40° C. tap water for 15 seconds. Then, 1.00 gram of the permanent waving lotion was applied to the tress. The tress was combed twice with the wide teeth on a comb. The permed tress was then placed on a tray at room temperature for 15 minutes. The tress was placed in a ZIPLOC® bag, and the bag was placed in a 50° C. oven for 10 minutes. The tress was rinsed for one minute under 40° C. tap water. 1.5 grams of the neutralizing solution was applied to the tress. The tress with the neutralizing solution on it was placed on a tray at room temperature for 5 minutes. The tress was then rinsed for one minute under 40° C. tap water and hung to air dry.

EXAMPLE VII

This example relates to the procedure used for evaluation of hair tresses prepared according to Examples V and VI by a sensory panel of volunteers. Prior to evaluation by a panelist, the hair tress is detangled by slowly combing through the tress with the large teeth of a comb to remove tangles. For dry combing evaluations, panelists are asked to comb slowly through the tress with the small teeth of a comb. The panelists are instructed to look for the amount of resistance. They are then instructed to rank the hair tresses in order from the best which is assigned a value of 1, to the worst which is assigned a value of 5, based on ease of combing. For dry feel evaluations, the panelists are instructed to slowly run their thumb and index finger along the hair tress. They are instructed again to look for the amount of resistance. The panelists rank the hair tresses in this scenario in order from the best (assigned a value of 1) to the worst (assigned a value of 5) based on feel of the dry tress.

Tables I and II below show results of such sensory panel evaluations on hair tresses treated with waving lotions and neutralizing solutions containing test materials A, C, D, and E.

"A" was the mercapto functional silicone containing emulsion prepared mechanically in Example IV according to procedures in EP 295780. Example IV replicates Examples 1 and 2 in EP 295780.

"B" was our CONTROL. It was the waving lotion and neutralizing solution in Example VI without any silicone.

"C" was our emulsion prepared by emulsion polymerization containing the branched mercapto functional silicone in Example II.

"D" was our emulsion prepared by emulsion polymerization containing the linear mercapto functional silicone in Example III.

"E" was an emulsion containing an amine functional silicone, the industry standard and benchmark, corresponding in general to the silicone composition described in U.S. Pat. No. 4,770,873 (Sep. 13, 1988).

TABLE I

Comparison of Dry Combing of Hair Treated With Various Permanent Waving Lotions and Neutralizing Solutions

| Panelist | A EP295780 | B Control | C Branched | D Linear | E Commercial |
|---|---|---|---|---|---|
| 1 | 5 | 4 | 1 | 3 | 2 |
| 2 | 5 | 4 | 2 | 1 | 3 |
| 3 | 5 | 4 | 1 | 3 | 2 |
| 4 | 4 | 5 | 1 | 2 | 3 |
| 5 | 5 | 3 | 1 | 4 | 2 |

TABLE II

Comparison of Dry Feel of Hair Treated With Various Permanent Waving Lotions and Neutralizing Solutions

| Panelist | A EP295780 | B Control | C Branched | D Linear | E Commercial |
|---|---|---|---|---|---|
| 1 | 5 | 4 | 1 | 2 | 3 |
| 2 | 5 | 4 | 1 | 2 | 3 |
| 3 | 5 | 4 | 1 | 2 | 3 |
| 4 | 4 | 5 | 1 | 2 | 3 |
| 5 | 5 | 4 | 1 | 3 | 2 |

It should be apparent from Table I, that with respect to Dry Combing, our "C" and "D" were better than Control "B" and "A" of EP 295780. Our "C" was better than industry benchmark "E", while our "D" was comparable to benchmark "E".

It should also be apparent from Table II, that with respect to Dry Feel, our "C" and "D" were each better than Control "B", "A" of EP 295780, and benchmark "E".

Other variations may be made in compounds, compositions, and methods described without departing from the essential features of our invention, the forms of which are exemplary and not limitations on the scope defined in the claims.

We claim:

1. In a process for permanent waving hair by a reaction in which cystine bridges are reduced to cysteine by applying to hair a waving lotion containing a reducing agent, the hair is reshaped, and the reaction is reversed by applying to hair a neutralizing solution containing an oxidizing agent, the improvement comprising incorporating into the waving lotion, the neutralizing solution, or in both the waving lotion and the neutralizing solution, an emulsion containing a mercapto functional silicone prepared by emulsion polymerization, the mercapto functional silicone having the formula $R'_{3-z}Q_zSiO[R_2'SiO]_x[R'QSiO]_ySiQ_zR'_{3-z}$ where $R'$ is an alkyl group of 1–4 carbon atoms or a phenyl group, provided at least 50 percent of the total number of $R'$ groups are methyl; $Q$ is mercapto functional substituent —$R''SH$ where $R''$ is a divalent alkylene radical of 3–6 carbon atoms; $z$ is 0 or 1; $x$ is 25–500; $y$ is 0–50 when $z$ is 1, and $y$ is 1–50 when $z$ is 0.

2. A process according to claim 1 in which the waving lotion and the neutralizing solution each further comprise a carrier fluid selected from the group consisting of water, alcohols, mixtures of water and alcohol, hydrocarbons, halogenated hydrocarbons, and volatile silicones.

3. A process according to claim 1 in which the reducing agent is thioglycolic acid.

4. A process according to claim 1 in which the oxidizing agent is hydrogen peroxide.

5. A process according to claim 1 in which the waving lotion and the neutralizing solution each contain 1.0–10.0 percent by weight of the mercapto functional silicone emulsion.

6. A process according to claim 5 in which the emulsion contains 10–70 percent by weight of mercapto functional silicone.

7. A process according to claim 6 in which the mercapto functional silicone is a linear polymer.

8. A process according to claim 6 in which the mercapto functional silicone is a branched polymer.

9. A process according to claim 7 in which the emulsion is an anionic or cationic emulsion.

10. A process according to claim 8 in which the emulsion is an anionic or cationic emulsion.

* * * * *